US008454990B2

(12) United States Patent
Canada et al.

(10) Patent No.: US 8,454,990 B2
(45) Date of Patent: *Jun. 4, 2013

(54) COMPOSITE ARTICLE SUITABLE FOR USE AS A WOUND DRESSING

(75) Inventors: T. Andrew Canada, Chesnee, SC (US); Martin E. Cowan, Moore, SC (US); Robert M. MacMeccan, Greer, SC (US); Le Zhang, Spartanburg, SC (US)

(73) Assignee: Milliken & Company, Spartanburg, SC (US)

(*) Notice: Subject to any disclaimer, the term of this patent is extended or adjusted under 35 U.S.C. 154(b) by 0 days.

This patent is subject to a terminal disclaimer.

(21) Appl. No.: 12/497,069

(22) Filed: Jul. 2, 2009

(65) Prior Publication Data

US 2010/0030171 A1    Feb. 4, 2010

Related U.S. Application Data

(60) Provisional application No. 61/085,596, filed on Aug. 1, 2008.

(51) Int. Cl.
*A61K 33/42*    (2006.01)

(52) U.S. Cl.
USPC .......................... 424/445; 424/604; 442/123

(58) Field of Classification Search
None
See application file for complete search history.

(56) References Cited

U.S. PATENT DOCUMENTS

| | | | |
|---|---|---|---|
| 3,975,567 A | 8/1976 | Lock | |
| 4,860,737 A | 8/1989 | Lang et al. | |
| 4,984,570 A * | 1/1991 | Langen et al. | 602/44 |
| 4,995,382 A | 2/1991 | Lang et al. | |
| 5,087,513 A * | 2/1992 | Kim | 442/118 |
| 5,208,098 A | 5/1993 | Stover | |
| 5,389,430 A | 2/1995 | Yilgör et al. | |
| 5,409,472 A | 4/1995 | Rawlings et al. | |
| 5,512,041 A | 4/1996 | Bogart | |
| 5,556,375 A | 9/1996 | Ewall | |
| 5,571,079 A | 11/1996 | Bello et al. | |
| 5,653,699 A | 8/1997 | Reed et al. | |
| 5,681,579 A | 10/1997 | Freeman | |
| 5,695,777 A | 12/1997 | Donovan et al. | |
| 5,782,787 A | 7/1998 | Webster | |
| 5,914,125 A | 6/1999 | Andrews et al. | |
| 5,914,282 A | 6/1999 | Dunshee et al. | |
| 5,947,917 A | 9/1999 | Carté et al. | |
| 5,973,221 A | 10/1999 | Collyer et al. | |
| 5,981,822 A | 11/1999 | Addison | |
| 6,013,275 A * | 1/2000 | Konagaya et al. | 424/443 |
| 6,051,747 A | 4/2000 | Lindqvist et al. | |
| 6,103,369 A | 8/2000 | Lucast et al. | |
| 6,103,951 A | 8/2000 | Freeman | |
| 6,180,052 B1 | 1/2001 | Ouellette et al. | |
| 6,191,335 B1 | 2/2001 | Robinson | |
| 6,207,875 B1 | 3/2001 | Lindqvist et al. | |
| 6,263,707 B1 * | 7/2001 | Miller et al. | 66/171 |
| 6,479,724 B1 | 11/2002 | Areskoug et al. | |
| 6,486,378 B1 | 11/2002 | Areskoug et al. | |
| 6,548,727 B1 | 4/2003 | Swenson | |
| 6,552,244 B1 | 4/2003 | Jacques et al. | |
| 6,566,575 B1 | 5/2003 | Stickels et al. | |
| 6,566,576 B1 | 5/2003 | Komerska et al. | |
| 6,566,577 B1 | 5/2003 | Addison et al. | |
| 6,765,123 B2 | 7/2004 | de Jong et al. | |
| 6,787,682 B2 | 9/2004 | Gilman | |
| 6,881,875 B2 | 4/2005 | Swenson | |
| 6,903,243 B1 | 6/2005 | Burton | |
| 6,977,323 B1 | 12/2005 | Swenson | |
| 6,986,270 B2 * | 1/2006 | Miller et al. | 66/202 |
| 7,022,890 B2 | 4/2006 | Sessions | |
| 7,161,056 B2 | 1/2007 | Gudnason et al. | |
| 7,220,889 B2 | 5/2007 | Sigurjonsson et al. | |
| 7,230,154 B2 | 6/2007 | Sigurjonsson | |
| 7,304,202 B2 | 12/2007 | Sigurjonsson et al. | |
| 7,622,629 B2 | 11/2009 | Aali | |
| 7,723,559 B2 | 5/2010 | Linnane et al. | |
| 7,759,537 B2 | 7/2010 | Bishop et al. | |
| 2002/0168400 A1 | 11/2002 | Jain | |
| 2003/0125685 A1 | 7/2003 | Swenson | |
| 2003/0161995 A1 | 8/2003 | Kauschke et al. | |
| 2004/0146717 A1 | 7/2004 | Corzani et al. | |
| 2004/0241214 A1 | 12/2004 | Kirkwood et al. | |
| 2004/0241215 A1 | 12/2004 | Lipman | |
| 2005/0035327 A1 * | 2/2005 | Canada et al. | 252/182.15 |
| 2005/0065486 A1 | 3/2005 | Fattman | |
| 2005/0182347 A1 | 8/2005 | Bishop et al. | |
| 2006/0067992 A1 | 3/2006 | Qin et al. | |
| 2006/0159732 A1 | 7/2006 | Cullen et al. | |
| 2006/0198993 A1 | 9/2006 | Goyarts | |
| 2007/0122462 A1 | 5/2007 | Chandra et al. | |

(Continued)

FOREIGN PATENT DOCUMENTS

| | | |
|---|---|---|
| EP | 0 541 251 A1 | 5/1993 |
| EP | 0 552 271 B1 | 4/1996 |

(Continued)

*Primary Examiner* — Hasan Ahmed
(74) *Attorney, Agent, or Firm* — Robert M. Lanning

(57) ABSTRACT

A composite article comprises a fluid transport layer, a fluid retentive layer, and, optionally, a moisture vapor permeable film. The first surface of the fluid transport layer provides a fluid contacting surface. The fluid retentive layer is positioned so that the first surface layer of the fluid retentive layer is adjacent to the second surface of the fluid transport layer. The moisture vapor permeable film is positioned so that it is adjacent to the second surface of the fluid retentive layer. The composite article is suitable for use as a wound dressing.

13 Claims, 2 Drawing Sheets

U.S. PATENT DOCUMENTS

| | | |
|---|---|---|
| 2007/0141130 A1 | 6/2007 | Villanueva et al. |
| 2007/0148432 A1 | 6/2007 | Baker et al. |
| 2007/0161936 A1 | 7/2007 | Svetlik |
| 2007/0161937 A1 | 7/2007 | Aali |
| 2007/0179210 A1 | 8/2007 | Swaniker |
| 2007/0179419 A1 | 8/2007 | Simpson |
| 2007/0191754 A1 | 8/2007 | Aali |
| 2007/0254974 A1 | 11/2007 | Mager et al. |
| 2007/0270730 A1 | 11/2007 | Rische et al. |

FOREIGN PATENT DOCUMENTS

| | | |
|---|---|---|
| EP | 0 788 874 A1 | 8/1997 |
| EP | 0 691 113 B1 | 7/2000 |
| EP | 1 401 362 B1 | 10/2006 |
| GB | 1 417 962 | 12/1975 |
| GB | 2 207 867 A | 2/1989 |
| GB | 2 253 628 A | 9/1992 |
| GB | 2 425 487 A | 11/2006 |
| GB | 2 430 443 A | 3/2007 |
| GB | 2 435 425 A | 8/2007 |
| WO | WO 90/10465 | 9/1990 |
| WO | WO 90/14109 | 11/1990 |
| WO | WO 2004/037115 A2 | 5/2004 |
| WO | WO 2005/115286 A1 | 12/2005 |
| WO | WO 2006/089551 A1 | 8/2006 |
| WO | WO 2006/094098 A2 | 9/2006 |
| WO | WO 2007/033678 A2 | 3/2007 |
| WO | WO 2007/068885 A2 | 6/2007 |

* cited by examiner

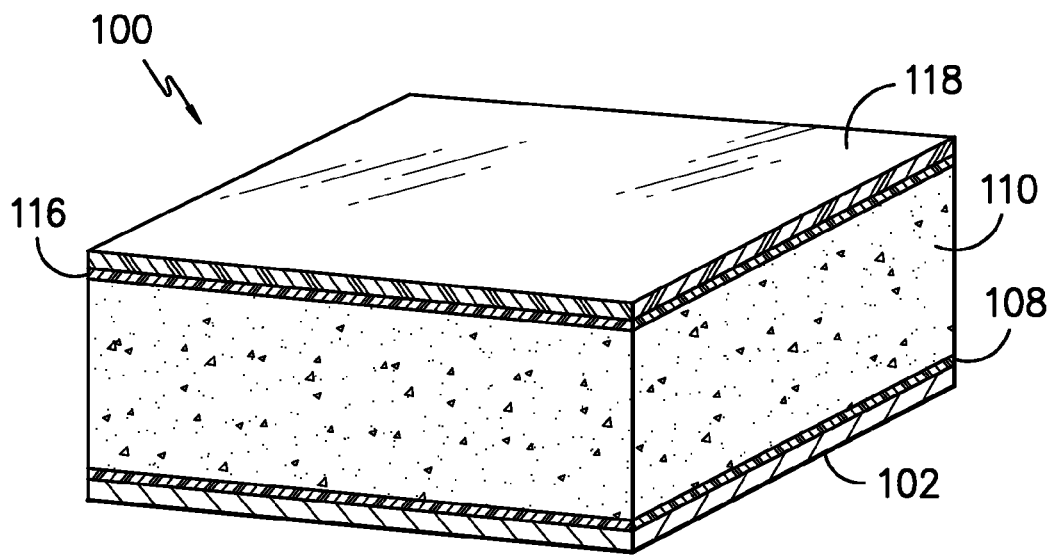
FIG. -1-
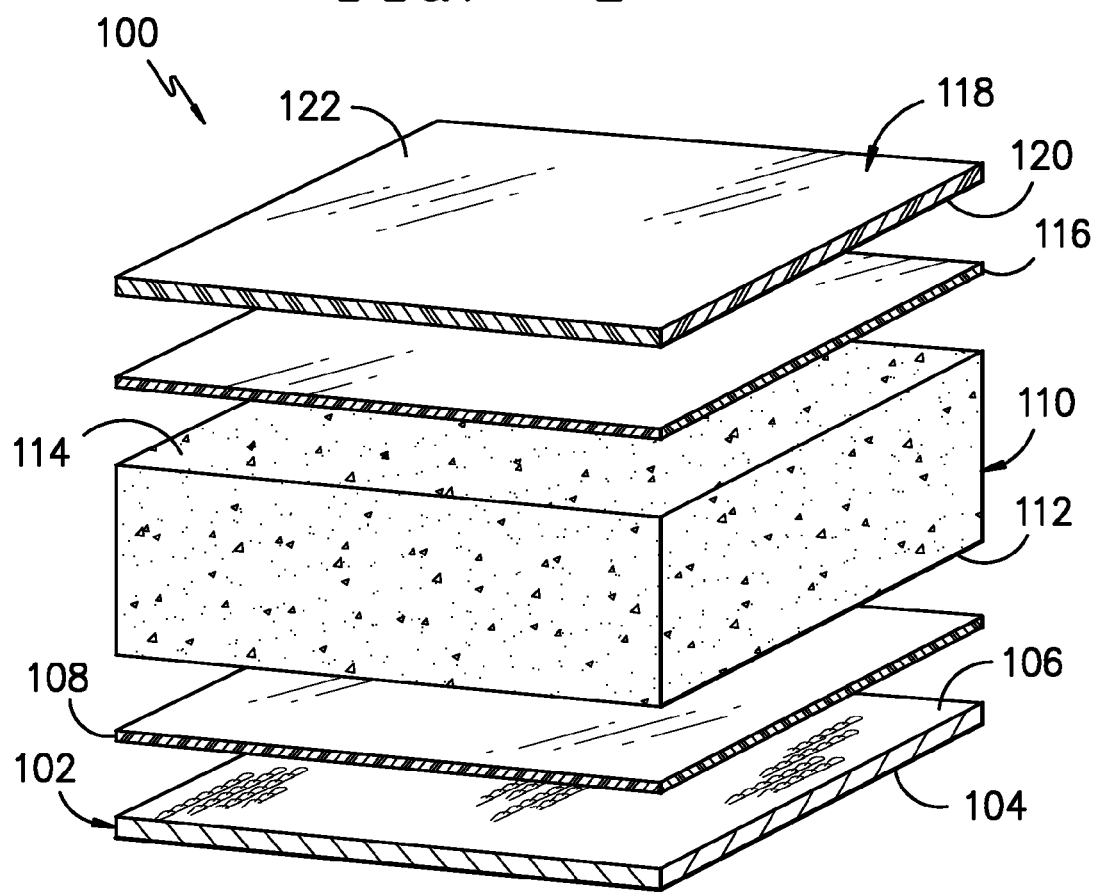
FIG. -1A-

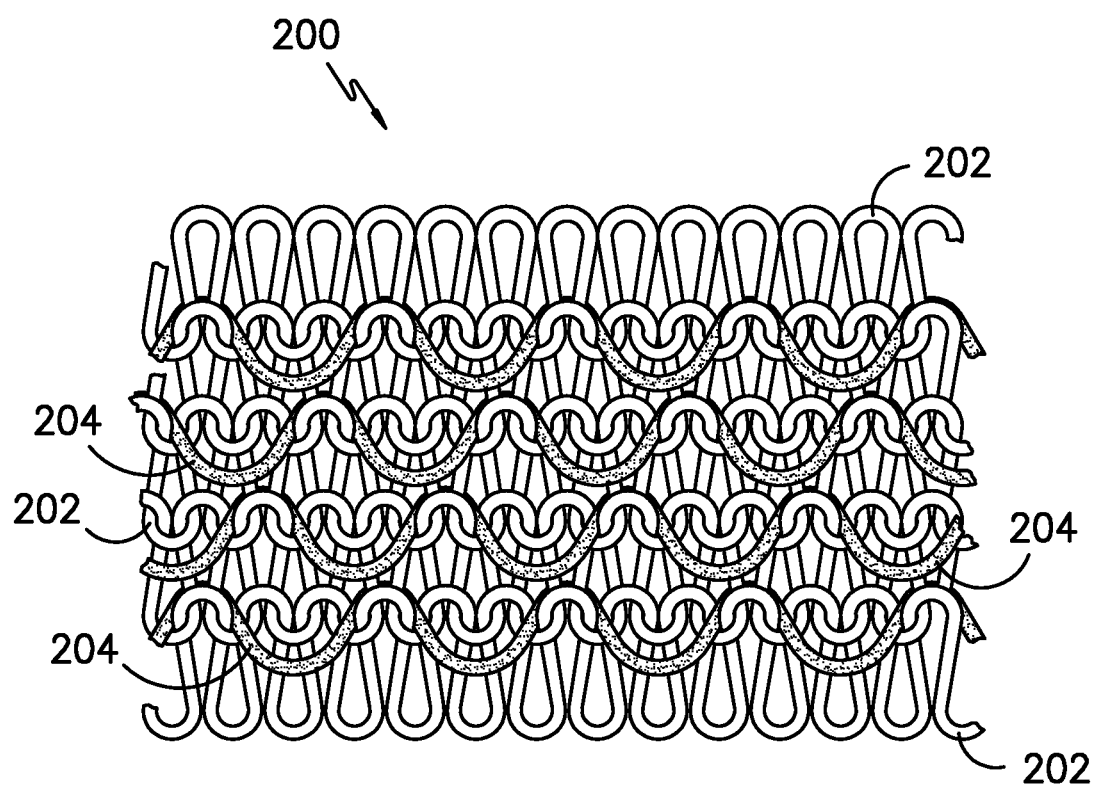
FIG. -2-

COMPOSITE ARTICLE SUITABLE FOR USE AS A WOUND DRESSING

CROSS-REFERENCE TO RELATED APPLICATIONS

This application claims, pursuant to 35 U.S.C. §119(e), the benefit of the filing date of U.S. Patent Application No. 61/085,596, which was filed on Aug. 1, 2008.

TECHNICAL FIELD OF THE INVENTION

The present invention is directed to composite articles exhibiting unique fluid transport properties. These fluid transport properties make the composite articles particularly suitable for use as wound dressings.

BACKGROUND

In the medical field, it is well-established that many factors affect the speed with which wounds heal. Among those factors, the amount of moisture present at the wound site has been found to be particularly important to the wound healing process. Generally speaking, excessive moisture at the wound site can lead to maceration, undesirable bacterial growth, and the production of protease enzymes. This bacterial growth can increase the potential for infection to occur, and the protease enzymes generated can damage tissue at the wound site. Thus, excessive moisture can hamper or delay the wound healing process.

Conversely, insufficient moisture at the wound site can deleteriously affect the wound healing process. Insufficient moisture at the wound site can cause scab or eschar formation and the generation of scar tissue. The formation of such tissues may cause any wound care device or medical dressing in contact with the wound to adhere to the wound. The removal of an adhered device or dressing can cause undue discomfort to the patient and can disrupt granulation tissue at the wound site. The removal of an adhered device or dressing can also leave pieces of the device or dressing imbedded in the wound. The presence of such debris can compound the risk of infection, especially if the wound and/or dressing are already colonized with pathogenic microbes.

A need therefore exists for an article that is suitable for use as a wound dressing and exhibits properties that permit the article to provide an environment suited to the promotion of wound healing. In particular, a need exists for an article that manages fluid (e.g., wound exudates) in such a way as to provide an environment that is sufficiently moist to promote the formation of granulation tissue and other wound-healing structures while also controlling the level of moisture in order to lessen the risk of maceration and the growth or proliferation of undesirable bacteria. The present invention seeks to provide such an article.

BRIEF SUMMARY OF THE INVENTION

In a first embodiment, the invention provides a composite article comprising a fluid transport layer and a fluid retentive layer. The fluid transport layer has a first surface and a second surface. The first surface of the fluid transport layer provides a fluid contacting surface having a first surface energy. The second surface of the fluid transport layer has a second surface energy. The fluid retentive layer has a first surface and a second surface, and the first surface of the fluid retentive layer has a third surface energy. The fluid retentive layer is positioned so that the first surface of the fluid retentive layer is adjacent to the second surface of the fluid transport layer. The surface energy of the first surface of the fluid retentive layer (i.e., the third surface energy) is greater than the surface energy of the second surface of the fluid transport layer (i.e., the second surface energy). In certain embodiments, such a composite article can comprise a moisture vapor permeable film. In those embodiments, the moisture vapor permeable film is positioned so that it is adjacent to the second surface of the fluid retentive layer.

In a second embodiment, the invention provides a wound dressing comprising a fluid transport layer, a fluid retentive layer, and a moisture vapor permeable film. The fluid transport layer has a first surface and a second surface. The first surface of the fluid transport layer provides a wound contacting surface having a first surface energy. The second surface of the fluid transport layer has a second surface energy. The fluid retentive layer has a first surface and a second surface, and the first surface of the fluid retentive layer has a third surface energy. The fluid retentive layer is positioned so that the first surface of the fluid retentive layer is adjacent to the second surface of the fluid transport layer. The moisture vapor permeable film is positioned so that it is adjacent to the second surface of the fluid retentive layer. The surface energy of the first surface of the fluid retentive layer (i.e., the third surface energy) is greater than the surface energy of the second surface of the fluid transport layer (i.e., the second surface energy).

In a third embodiment, the invention provides a composite article comprising a fluid transport layer and a fluid retentive layer. The fluid transport layer has a first surface and a second surface. The first surface of the fluid transport layer provides a fluid contacting surface having a first surface energy. The second surface of the fluid transport layer has a second surface energy. The fluid retentive layer has a first surface and a second surface, and the first surface of the fluid retentive layer has a third surface energy. The fluid retentive layer is positioned so that the first surface of the fluid retentive layer is adjacent to the second surface of the fluid transport layer. The surface energy of the first surface of the fluid transport layer (i.e., the first surface energy) is greater than the surface energy of the second surface of the fluid transport layer (i.e., the second surface energy), and the surface energy of the second surface of the fluid transport layer (i.e., the second surface energy) is greater than the surface energy of the first surface of the fluid retentive layer (i.e., the third surface energy). In certain embodiments, such a composite article can comprise a moisture vapor permeable film. In those embodiments, the moisture vapor permeable film is positioned so that it is adjacent to the second surface of the fluid retentive layer.

BRIEF DESCRIPTION OF THE DRAWINGS

FIG. 1 is a perspective view of a composite article according to the invention.

FIG. 1A is an exploded, perspective view of the composite article depicted in FIG. 1.

FIG. 2 is a plan view of a laid-in fabric suitable for use as the fluid transport layer of a composite article according to the invention.

DETAILED DESCRIPTION OF THE INVENTION

As utilized herein, the term "surface energy" refers to the excess energy at the surface of a material compared to the bulk of the material (e.g., the interior portions of the material) and is usually expressed in terms of milliJoules per square meter ($mJ/m^2$). The surface energy quantifies the disruption of intermolecular bonds that occurs when a surface is created. The surface energy can be measured by several means including, for example, the Fowkes method. In this method, two reference liquids are used to first measure the dispersive component and the polar component of the material's surface energy. The surface energy of the material is then calculated from the measured dispersive and polar components. In general, a surface having a higher surface energy will exhibit a higher affinity for aqueous fluids, such as perspiration or wound exudate.

In a first embodiment, the invention provides a composite article comprising a fluid transport layer, a fluid retentive layer, and, optionally, a moisture vapor permeable film. As depicted in FIG. 1 and FIG. 1A, the composite article 100 comprises a fluid transport layer 102. The fluid transport layer 102 has a first surface 104, which provides a fluid-contacting surface for the composite article 100, and a second surface 106. The fluid retentive layer 110 has a first surface 112 and second surface 114 and is positioned so that the first surface 112 is adjacent to the second surface 106 of the fluid transport layer 102. Thus, the fluid retentive layer 110 can act as a reservoir for the fluids taken up by the fluid transport layer 102. The composite article 100 can also comprise a moisture vapor permeable film 118, which is positioned so that it is adjacent to the second surface 114 of the fluid retentive layer 110. As depicted in FIG. 1 and FIG. 1A, the fluid transport layer, fluid retentive layer, and, if present, moisture vapor permeable film can be attached to each other using adhesive layers 108, 116.

The fluid transport layer of the composite article can be any suitable material that is capable of absorbing fluids that contact the fluid-contacting surface of the layer (i.e., the first surface 104 of the fluid contacting layer 102) and transporting or wicking those fluids away from the fluid-contacting surface. In a specific embodiment, the fluid transport layer can be a textile material, such as a textile material selected from the group consisting of knit textiles, woven textiles, and non-woven textiles.

As noted above, the fluid transport layer 102 comprises a first surface 104 and a second surface 106. The first surface 104 of the fluid transport layer 102 has a first surface energy, and the second surface 106 of the fluid transport layer 102 has a second surface energy. In certain embodiments, the surface energy of the first surface 104 of the fluid transport layer 102 and the surface energy of the second surface 106 of the fluid transport layer 102 can be substantially the same. In a specific embodiment, the surface energy of the second surface 106 of the fluid transport layer 102 is greater than the surface energy of the first surface 104 of the fluid transport layer 102. This difference in surface energies between the two surfaces means that the second surface 106 of the fluid transport layer 102 exhibits a greater affinity for aqueous fluids (e.g., perspiration or wound exudates) than the first surface 104 of the fluid transport layer 102. Thus, any aqueous fluids absorbed by the fluid transport layer 102 will be transported or pumped from the first surface 104 to the second surface 106 of the fluid transport layer 102. This active transportation or pumping of the fluids ensures that excess moisture does not accumulate at the interface of fluid transport layer 102 and a fluid exuding surface, such as the skin or an exuding wound.

When the fluid transport layer comprises first and second surfaces having different surface energies, the difference between the two surface energies can be of any suitable magnitude. In a specific embodiment, the surface energy of the second surface 106 of the fluid transport layer 102 can be about 101% or more of the surface energy of the first surface 104 of the fluid transport layer 102. In more specific embodiments, the surface energy of the second surface 106 can be about 102% or more, about 103% or more, or about 104% or more of the surface energy of the first surface 104.

In a specific embodiment, the fluid transport layer 102 can be a textile material in which the surface energy of the second surface 106 is higher than the surface energy of the first surface 104. In such an embodiment, the textile material can be selected from the group consisting of knit textiles, woven textiles, and non-woven textiles. Suitable knit textiles include, but are not limited to, weft-knit textiles, such as flat-knit textiles and circular-knit textiles. One embodiment of such a fluid transport layer is depicted in FIG. 2.

As depicted in FIG. 2, the fluid transport layer 200 can be a laid-in fabric comprising one or more yarns 202 providing the knit structure of the fabric and one or more effect yarns 204 tucked into the fabric structure. In order to provide two surfaces having different surface energies, the fluid transport layer 200 depicted in FIG. 2 is a jersey knit fabric in which the effect yarn(s) 204 are incorporated into the fabric structure so that the effect yarn(s) 204 are predominantly present on the technical back of the fabric structure. In other words, the effect yarn(s) 204 are incorporated in the fabric structure so that most of the effect yarn(s) 204 (e.g., most of the surface area of the effect yarn(s)) is present on the technical back of the fabric structure. Such a construction results in a fabric in which the technical face of the fabric is predominantly one type of yarn 202, and the technical back presents a higher proportion of the effect yarn(s) 204. Thus, when the yarn 202 and the effect yarn 204 have different surface energies or one is more hydrophilic than the other, the resulting fabric will exhibit a different surface energy on each of the two major surfaces. In a specific embodiment of the fluid transport layer depicted in FIG. 2, the yarn(s) 202 are more hydrophilic than the effect yarn(s) 204. For example, the yarn(s) 202 can be polyamide yarns (e.g., nylon yarns), and the effect yarn(s) 204 can be polyester yarns. Such an embodiment of the fluid transport layer provides a layer in which the technical face of the fabric exhibits a higher surface energy than the technical back of the fabric. Thus, when utilized as the fluid transport layer of the composite article depicted in FIG. 1 and FIG. 1A, such a fabric (i.e., the fabric depicted in FIG. 2) is disposed so that the technical back of the fabric forms the first surface 104 of the fluid transport layer 102 and the technical face of the fabric forms the second surface 106 of the fluid transport layer 102.

A fluid transport layer such as that depicted in FIG. 2 can further comprise yarns or fibers that provide the layer with the ability to be stretched and then return to dimensions that are substantially the same as its original dimensions. For example, in addition to the components noted above, the yarn(s) 202 can further comprise elastomeric fibers, or the fluid transport layer can further comprise elastomeric fibers or yarns that are "parallel" to the yarn(s) 202 (i.e., the elastomeric yarns or fibers are incorporated into the knit structure so that they run alongside the yarn(s) 202). Alternatively, in addition to the effect yarn(s) 204, the fabric can include elastomeric yarn(s) or stretch yarn(s) that have been tucked into the fabric structure. In a specific embodiment, the fluid transport layer comprises an elastomeric yarn, such as a Spandex yarn (i.e., a manufactured fiber in which the fiber-forming substance is a long chain synthetic polymer composed of at least 85% of a segmented polyurethane).

In order to provide the differential surface energies described above, the fluid transport layer can also comprise a material in which one surface has been chemically or physically modified to yield a material having first and second surfaces exhibiting different surface energies. For example, in one embodiment, the fluid transport layer can be a textile material such as those described above having a first surface that has been chemically treated in order to lower the surface energy thereof. In such an embodiment, the textile material can be treated, for example, with a relatively hydrophobic fluorocarbon or silicone (i.e., a fluorocarbon or silicone that is more hydrophobic than the material comprising the non-treated side of the textile material). In order to ensure that the use of such treatments does not produce a surface that is non-absorbent, the chemical or physical modifications can be applied in such a manner as to produce a surface comprising a plurality of discrete discontinuities in the treatment. These discontinuities provide a path for fluid to by-pass the modified surface of the fluid transport layer, where the differential surface energies then transport or pump the fluid through the fluid transport layer and into the fluid retentive layer.

The fluid transport layer of the composite article can exhibit any suitable absorptive capacity. For example, the fluid transport layer can exhibit a fluid absorption (e.g. water absorption) of about 100 wt. % or more based on the weight of the fluid transport layer. In a specific embodiment, the fluid transport layer can exhibit a fluid absorption (e.g., water absorption) of about 150 wt. % or more, about 200 wt. % or more, or about 250 wt. % or more based on the weight of the fluid transport layer.

The fluid retentive layer of the composite article can be any suitable material that is capable of retaining or absorbing fluids transported to the surface of the fluid retentive layer by the fluid transport layer. For example, the fluid retentive layer can be selected from the group consisting of foams, textile materials (e.g. woven, knit, and nonwoven textile materials), alginates, superabsorbent polymers, gels (e.g., hydrogels), and combinations or mixtures thereof. The fluid retentive layer can also comprise a combination of two or more discrete layers, which layers can comprise any of the absorptive materials listed above. In a specific embodiment, the fluid retentive layer 110 can be a foam, such as an open cell, non-reticulated polymer foam. Such foams can be made from any suitable material including, but not limited to, polyurethane polymers. In order to provide a fluid retentive layer exhibiting the requisite surface energy (i.e., a surface energy that is higher than the surface energy of the adjacent surface of the fluid transport layer), a polyurethane polymer used in making such a foam can be a polyester-based polyurethane polymer (i.e., a polyurethane polymer made from a reaction mixture containing a polyester polyol).

The fluid retentive layer of the composite article can exhibit any suitable absorptive capacity. For example, the fluid retentive layer can exhibit a fluid absorption of about 100 wt. % or more based on the weight of the fluid retentive layer. In a specific embodiment, the fluid retentive layer can exhibit a fluid absorption of about 200 wt. % or more, about 300 wt. % or more, about 400 wt. % or more, about 500 wt. % or more, about 600 wt. % or more, about 700 wt. % or more, about 800 wt. % or more, about 900 wt. % or more, or about 1000 wt. % or more based on the weight of the fluid retentive layer. The absorptive capacity of the fluid retentive layer can be measured by any suitable means. For example, the absorptive capacity of the fluid retentive layer can be measured by immersing a known weight of the fluid retentive layer in phosphate-buffered saline containing 0.9 wt. % sodium chloride at 37° C. for 30 minutes.

As noted above and depicted in FIG. 1 and FIG. 1A, the fluid retentive layer optionally comprises a first surface 112 and is positioned so that the first surface 112 is adjacent to the second surface 106 of the fluid transport layer 102. The first surface 112 of the fluid retentive layer 110 exhibits a surface energy. In order to facilitate the transport of aqueous fluids from the fluid transport layer 102 to the fluid retentive layer 110, the surface energy of the first surface 112 of the fluid retentive layer 110 is greater than the surface energy of the second surface 106 of the fluid transport layer 102. By utilizing a fluid retentive layer 110 having a surface energy that is greater than the surface energy of the second surface 106 of the fluid transport layer 102, the fluid retentive layer 110 exhibits a greater affinity for aqueous fluids than the fluid transport layer. The resulting composite therefore is capable of transporting fluid from the fluid transport layer to the fluid retentive layer. Moreover, due to the difference in surface energies and affinity for aqueous fluids, the composite is capable of transporting this fluid below the saturation point of the fluid transport layer (i.e., before the fluid transport layer becomes saturated with the fluid). When the composite article is used as a wound dressing, this ability can significantly reduce the risks of maceration associated with exuding wounds.

The difference between the surface energy of the first surface 112 of the fluid retentive layer 110 and the second surface 106 of the fluid transport layer 102 can be of any suitable magnitude. For example, the surface energy of the first surface 112 of the fluid retentive layer 110 can be about 105% or more of the surface energy of the second surface 106 of the fluid transport layer. In a specific embodiment, the surface energy of the first surface 112 of the fluid retentive layer 110 can be about 110% or more, about 115% or more, about 120% or more, or about 125% or more of the surface energy of the second surface 106 of the fluid transport layer.

As noted above and depicted in FIG. 1 and FIG. 1A, the composite article 100 optionally comprises a moisture vapor permeable film 118. When present, the moisture vapor permeable film 118 is positioned so that the first surface 120 of the moisture vapor permeable film 118 is adjacent to the second surface 114 of the fluid retentive layer 110. In the embodiment depicted in FIG. 1 and FIG. 1A, the second surface 122 of the moisture vapor permeable film 118 provides a top, occlusive surface for the composite article 100 that helps to prevent foreign matter (e.g., fluids, dirt, microbes, etc.) from entering the composite article.

The moisture vapor permeable film can be any suitable material that is permeable to water vapor and capable of providing the occlusive surface noted above. The moisture vapor permeable film can be selected from polyurethane films, polyamide block copolymer films, and polyester block copolymer films. In a specific embodiment, the moisture vapor permeable film can be a polyurethane film, such as a polyether-based polyurethane film or polyester-based polyurethane film.

The moisture vapor permeable film can have any suitable moisture vapor transmission rate (MVTR). More specifically, the moisture vapor permeable film typically exhibits an MVTR that is high enough to prevent the composite article from becoming saturated when it is placed in contact with, for example, a moderately-exuding wound. However, the moisture permeable film typically does not exhibit an MVTR that is so high that the composite article will be completely dry when it is placed in contact with, for example, a lightly-exuding or non-exuding wound. In a specific embodiment, the moisture vapor permeable film exhibits an MVTR of about 500 $g/m^2/24$ hr or more, about 1,000 $g/m^2/24$ hr or more, about 5,000 $g/m^2/24$ hr or more, or about 10,000 $g/m^2/24$ hr or more (e.g., about 12,000 $g/m^2/24$ hr), when measured in accordance with ASTM Standard E-96 entitled "Standard Test Methods for Water Vapor Transmission of Materials" using an upright cup method.

As depicted in FIG. 1 and FIG. 1A, the adjacent surfaces of the fluid transport layer 102, the fluid retentive layer 110, and, when present, the moisture vapor permeable film 118 can be adhered to each other using one or more suitable adhesives 108, 116. In such an embodiment, the adhesives help to provide a coherent, dimensionally stable composite article and prevent delamination of the layers upon removal of the composite article. The adhesive(s) used in the composite can be any suitable adhesive(s). Suitable adhesives include, but are not limited to, solvent-based adhesives, latex adhesives, pressure-sensitive adhesives, hot-melt adhesives, and reactive adhesives. Suitable pressure-sensitive adhesives include, but are not limited to, pressure-sensitive adhesives made from acrylics, natural latexes, styrene-butadiene rubbers, and reclaimed rubbers. Suitable hot-melt adhesives include, but are not limited to, polyamides, polyolefins, and poly(ethylene-co-vinyl acetate).

As noted above, the adhesive layers 108,116 can be any suitable adhesive. In a specific embodiment, the adhesive layer 108 can be a hot-melt adhesive, such as those hot-melt adhesives listed in the foregoing paragraph. In a more specific embodiment, the adhesive layer 108 can be a polyamide hot-melt adhesive. In order to ensure that the adhesive layer 108 does not act as an occlusive layer preventing the transport of fluid from the fluid transport layer 102 to the fluid retentive layer 110, the adhesive comprising the adhesive layer 108 can be applied in a pattern covering only a portion of the area between the adjacent surfaces of the fluid transport layer 102 and the fluid retentive layer 110. The amount of coverage provided by the adhesive can be any suitable amount that provides sufficient adhesion of the fluid transport layer 102 and the fluid retentive layer 110 (i.e., sufficient adhesion to prevent delamination of the layers during use of the composite article) without preventing the transport of fluid between the two layers. For example, the adhesive 108 can be provided in a suitable pattern covering about 10% to about 98% of the area between the fluid transport layer 102 and the fluid retentive layer 110. In a specific embodiment, the adhesive 108 can be a polyamide hot-melt adhesive web providing, for example, about 10% to about 98% coverage of the area between the fluid transport layer 102 and the fluid retentive layer 110.

When present, the adhesive can be applied to the layers of the composite article in any suitable amount. The adhesive typically is present in or applied to the composite article in an amount sufficient to prevent partial or complete delamination of the layers of the composite article without negatively impacting the fluid transport properties of the composite article. Also, the amount of adhesive required to provide a composite article having the desired physical properties may vary based upon the particular adhesive(s) used. In a specific embodiment, such as when the adhesive is a hot-melt adhesive (e.g., a polyamide hot-melt adhesive), the adhesive can be present in the composite article in an amount of about 3 g/m$^2$ or more (about 0.1 oz/yd$^2$ or more), about 17 g/m$^2$ or more (about 0.5 oz/yd$^2$ or more), about 34 g/m$^2$ or more (about 1 oz/yd$^2$ or more), about 50 g/m$^2$ or more (about 1.5 oz/yd$^2$ or more), about 100 g/m$^2$ or more (about 3 oz/yd$^2$ or more), or about 340 g/m$^2$ or more (about 10 oz/yd$^2$ or more).

In a specific embodiment, the adhesive layer 116 between the fluid retentive layer 110 and the moisture vapor permeable film 118 can be a pressure-sensitive adhesive, such as those pressure-sensitive adhesives listed in the preceding paragraph. In a more specific embodiment, the adhesive layer 116 is an acrylic pressure-sensitive adhesive. As with the adhesive layer 108 between the fluid transport layer 102 and the fluid retentive layer 110, the adhesive comprising the adhesive layer 116 can be applied in a pattern covering only a portion of the area between the adjacent surfaces of the fluid retentive layer 110 and the moisture vapor permeable film 118. Once again, the amount of adhesive applied should be sufficient to prevent delamination of the fluid retentive layer 110 and the moisture vapor permeable film 118 without preventing the transmission of moisture vapor through the moisture vapor permeable film 118.

In an alternative embodiment, the moisture vapor permeable film 118 can be laminated onto the second surface 114 of the fluid retentive layer 110. In such an embodiment, the moisture vapor permeable film can be laminated onto the fluid retentive layer by heating the film to a temperature sufficient to at least partially melt the polymer(s) from which it is made, pressing the film onto the fluid retentive layer, and then allowing the film to cool to a temperature sufficient for the polymer(s) from which the film is made to solidify. In this embodiment, the heated film should be pressed onto the fluid retentive layer using a pressure sufficient to ensure that physical bonds between the film and fluid retentive layer are formed once the film cools and solidifies.

In certain embodiments, the composite article can further comprise an apertured film positioned so that the apertured film is adjacent to the first surface of the fluid transport layer. Such an apertured film can be comprised of any suitable material. In certain embodiments, the apertured film can be comprised of a material having a surface energy that is lower than the surface energy of the first surface of the fluid transport layer. In such an embodiment, the apertures provided in the film allow fluid to pass through the apertured film and into the fluid transport layer, while the relatively low surface energy exhibited by the film establishes a surface energy gradient that functions to transport or pump fluid away from the apertured film and through the fluid transport layer. In a specific embodiment, the apertured film can be made from a polymer selected from the group consisting of polyolefins, polyesters, and polyamides. In certain embodiments, the apertured film can be a polyolefin film, such as the Delnet® apertured films available from DelStar Technologies, Inc. The apertures in the apertured film can be of any suitable size and shape, provided the apertures allow fluid to pass through the apertured film and into the fluid transport layer. For example, the apertured film can comprise apertures provided in the shape of slits, circles, hexagons, triangles, and the like.

The composite article can further comprise one or more active ingredients. These active ingredients can be incorporated into one or more of the layers of the composite article, or they can be applied as a surface coating on or between one or more of the layers of the composite article. Actives suitable for use in the composite article include, but are not limited to, antimicrobial agents, antibiotics, analgesics, moisturizers (e.g., glycerin, urea, lactic acid, etc.), humectants, debriders (e.g., enzymatic debriders), matrix metalloproteinase inhibitors, growth factors, and combinations thereof. Suitable antimicrobial agents include, but are not limited to, silver-based antimicrobials, such as silver ion exchange materials (e.g., silver zirconium phosphates, silver calcium phosphates, silver zeolites, etc.), silver particles (e.g., metallic silver, nanosilver, colloidal silver, etc.), silver salts (e.g., AgCl, $Ag_2CO_3$, etc.), silver glass, and combinations thereof. In a specific embodiment, the antimicrobial agent can be a silver ion exchange material such as a silver sodium hydrogen zirconium phosphate. Suitable antimicrobial agents also include, but are not limited to, antimicrobial compounds containing copper, zinc, iodine, 5-chloro-2-(2,4-dichlorophenoxy)phenol), polyhexamethylene biguanide (PHMB), N-halamines, chlorhexidine, quaternary ammonium complexes, and combinations and mixtures thereof. Antimicrobial agents suitable for use in the composite article also include combinations of silver-based antimicrobials (e.g., silver ion exchange materials) and non-silver-based antimicrobials.

In order to actively mitigate the risk of infection when the composite is used as a wound dressing, the fluid transport layer 102 can, in a specific embodiment, comprise one or more antimicrobial agents. The antimicrobial agent(s) can be incorporated into the material forming the fluid transport layer. For example, when the fluid transport layer is a textile material such as that depicted in FIG. 2, the antimicrobial agent(s) can be incorporated into the fibers or yarns forming the textile material. Alternatively, the antimicrobial agent(s) can be applied to the fluid transport layer in the form of a coating. In a specific embodiment, the fluid transport layer can comprise a coating applied to one or more surfaces of the fluid transport layer, the coating comprising one or more antimicrobial agents and a suitable binder. The binder used in such a coating can be any suitable binder, such as a polyurethane binder. In a more specific embodiment, the fluid transport layer can be a textile material such as that depicted in FIG. 2 further comprising a coating applied to both surfaces of the textile material. In such an embodiment, the coating can comprise a polyurethane binder and a silver-based antimicrobial, such as a silver sodium hydrogen zirconium phosphate. In such an embodiment, the antimicrobial can be applied to the fluid transport layer in an amount of about 10 to about 20 wt. % based on the weight of the fluid transport layer using about 2 to about 6 wt. % of a polyurethane binder.

In another embodiment, one or more antimicrobial agents can be applied to or incorporated into the fluid retentive layer. For example, when the fluid retentive layer is a polymer foam, one or more suitable antimicrobial agents can be incorporated into the reaction mixture used to form the polymer foam, thereby providing a polymer foam having the antimicrobial agent(s) incorporated throughout the polymer foam. In a specific embodiment, the fluid retentive layer 110 can be a polymer foam (e.g., a polyether-based polyurethane foam) comprising a silver-based antimicrobial agent (e.g., a silver sodium hydrogen zirconium phosphate antimicrobial) dispersed or incorporated throughout the polymer foam.

In order to secure the composite article in place during use, the composite article can, in certain specific embodiment, comprise a layer of adhesive on the fluid-contacting surface (i.e., first surface) of the fluid transport layer. The adhesive can be applied over the entire area of the fluid-contacting surface of the fluid transport layer, or the adhesive layer can be applied to only a portion of the area. For example, the adhesive can be applied to the perimeter of the fluid transport layer, thereby providing a means for the composite article to be adhered to the surface (e.g., skin) without affecting the fluid transport properties of the bulk of the fluid transport layer. The adhesives suitable for use in such a composite article include, but are not limited to, the pressure-sensitive adhesives described above in the discussion of the adhesive layers 108, 116.

While the composite article in FIG. 1 and FIG. 1A has been depicted as comprising layers that are coextensive with adjacent layers, the layers need not be coextensive, provided they are arranged as described above. In one embodiment, for example, the moisture vapor permeable film can have a greater area than the fluid transport layer and the fluid retentive layer. Such a composite article would comprise an "excess" of the moisture vapor permeable film extending beyond the perimeter of the fluid transport layer and the fluid retentive layer. Further, this "excess" can, in certain embodiments, be coated with a pressure-sensitive adhesive (such as those described above) in order to provide a means for the composite article to be secured in place during use. In another embodiment, the fluid retentive layer can comprise a plurality of discrete, non-continuous "islands" positioned between the fluid transport layer and the moisture vapor permeable film. These "islands" can be formed from any of the materials listed in the discussion of the fluid retentive layer, including polymer foams.

The composite article can be provided in any shape or form suitable for its intended use. For example, the composite article can be provided in the shape of a rectangle, square, circle, heart, or butterfly in order to provide an article suitable for use in dressing a particular wound or location of wound. Furthermore, the perimeter of the composite article can be tapered so that the profile of the composite article is thinner at its perimeter. This embodiment of the composite article can be produced, for example, by using a fluid retentive layer having a thinner profile at its perimeter. Such a composite article would provide a less harsh profile when used as a wound dressing, which should increase patient comfort.

The composite article of the invention can be provided in any suitable dimensions. For ease of wearing and patient comfort when used as a wound dressing, the composite article typically is about 1 cm or less in thickness, preferably about 50 mm or less in thickness. In order to provide an article that is capable of managing a moderate amount of fluid (e.g., wound exudates), the composite article typically is about 0.5 mm or more in thickness. In a specific embodiment, the composite article is from about 1 mm to about 20 mm in thickness, or from about 5 mm to about 10 mm (e.g., about 5 mm to about 8 mm) in thickness.

As noted throughout this specification, the composite article of the invention is believed to be particularly well-suited for use as a wound dressing. Thus, in a second embodiment, the invention provides a wound dressing having the structure described above for the first embodiment of the composite article of the invention. When used as a wound dressing, the composite article typically is positioned so that the first surface of the fluid transport layer is closest to the skin of the patient. When this surface of the composite article exhibits a lower surface energy than the fluid retentive layer, the aqueous fluids (e.g., wound exudate or perspiration) absorbed by the fluid transport layer will be transported from this layer into the fluid retentive layer. Also, as noted above, such a gradient of surface energies among the layers of the composite article allows these aqueous fluids to be transported to the fluid retentive layer before the fluid transport layer becomes saturated. Once in the fluid retentive layer, the aqueous fluids can then evaporate, for example, through the moisture vapor permeable film. It is believed that these active fluid management properties provide a wound dressing that is capable of maintaining an environment that is sufficiently moist to promote wound healing while also maintaining an environment that is not so moist as to cause maceration of the skin and the proliferation of bacteria.

In a third embodiment, the composite article of the invention can also comprise a fluid transport layer and a fluid retentive layer, as described above and depicted in FIG. 1 and FIG. 1A. However, in this embodiment, the surface energy of the first surface 104 of the fluid transport layer 102 is greater than the surface energy of the second surface 106 of the fluid transport layer 102, and the surface energy of the second surface 106 of the fluid transport layer 102 is greater than the surface energy of the first surface 112 of the fluid retentive layer 110. This gradient in surface energies means that the second surface 106 of the fluid transport layer 102 exhibits a greater affinity for aqueous fluids than the first surface 112 of the fluid retentive layer 110 and the first surface 104 of the fluid transport layer 102 exhibits a greater affinity for aqueous fluids than the second surface 106 of the fluid transport layer 102. Thus, in this embodiment, the composite article 100 is able to transport or pump fluid from the fluid retentive layer 110 to the fluid transport layer 102. Applicants believe that this embodiment of the composite article can be particularly useful in the treatment of dry wounds, which require supplemental moisture in order to promote more effectively healing of the wound. Applicants also believe that this embodiment of the composite article can be particularly effective for the delivery of one or more of the active ingredients described above. In particular, Applicants believe that the article's ability to actively transport or pump fluid to the wound site can also provide an effective means to deliver one or more active ingredients to the wound site, especially those active ingredients that are soluble in or exhibit an affinity for aqueous fluids.

The fluid transport layer, fluid retentive layer, and, if present, moisture vapor permeable film used in the third embodiment of the composite article can be the same as those described above for the first embodiment of the composite article, provided the materials are selected to provide the surface energy gradient described above. In a specific embodiment of such a composite article, the fluid transport layer can be a textile material such as that depicted in FIG. 2 and described above. However, in order to provide the appropriate surface energy gradient, the textile material can be positioned within the composite article so that the technical face of the textile material (i.e., the face of the textile material comprising a predominance of yarns 202) provides the contact surface of the composite article (e.g., the wound contacting surface of the composite article).

In the third embodiment of the composite article of the invention, the difference between the surface energy of the first surface of the fluid transport layer and the surface energy of the second surface of the fluid transport layer can be of any suitable magnitude. In a specific embodiment, the surface energy of the first surface 104 of the fluid transport layer 102 can be about 101% or more of the surface energy of the second surface 106 of the fluid transport layer 102. In more specific embodiments, the surface energy of the first surface 104 can be about 102% or more, about 103% or more, or about 104% or more of the surface energy of the second surface 106.

As with the first embodiment of the composite article of the invention, the third embodiment of the composite article of the invention can be provided in any suitable shape, including those listed above. Also, while the various layers of the composite article have been depicted as being coextensive with adjacent layers, the layers of the composite article need not be coextensive with the adjacent layers, provided the layers are arranged as described above. Furthermore, the third embodiment of the composite article of the invention can be provided in any suitable dimensions, including those listed above.

As noted above, Applicants believe that the third embodiment of the composite article of the invention (i.e., the embodiment in which the first surface of the fluid transport layer has the highest surface energy) can be particularly useful in the treatment of dry wounds. For example, such an embodiment of the composite article can be placed onto the wound in a moistened state (e.g., the fluid retentive layer can be moistened so that it contains fluid available for transport to the wound through the fluid transport layer) so that the composite article will actively transport or pump fluid to the dry wound, thereby providing a moist environment better suited to wound healing. When used in this manner, the composite article can be packaged in a pre-moistened state, or the composite article can be provided in a dry state that is wet before application to the wound site.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the subject matter of this application (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the subject matter of the application and does not pose a limitation on the scope of the subject matter unless otherwise claimed. No language in the specification should be construed as indicating any non-claimed element as essential to the practice of the subject matter described herein.

Preferred embodiments of the subject matter of this application are described herein, including the best mode known to the inventors for carrying out the claimed subject matter. Variations of those preferred embodiments may become apparent to those of ordinary skill in the art upon reading the foregoing description. The inventors expect skilled artisans to employ such variations as appropriate, and the inventors intend for the subject matter described herein to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

What is claimed is:

1. A composite article comprising:
   (a) a fluid transport layer, the fluid transport layer having a first surface and a second surface, the first surface of the fluid transport layer providing a fluid contacting surface having a first surface energy, and the second surface of the fluid transport layer having a second surface energy,
   (b) a fluid retentive layer, the fluid retentive layer having a first surface and a second surface, the first surface of the fluid retentive layer having a third surface energy, and the fluid retentive layer being positioned so that the first surface of the fluid retentive layer is adjacent to the second surface of the fluid transport layer; and
   (c) a moisture vapor permeable film, the moisture vapor permeable film being positioned so that it is adjacent to the second surface of the fluid retentive layer, the moisture vapor permeable film exhibiting a moisture vapor transmission rate (MVTR) of about 500 g/m$^2$/24 hr or more;

wherein the third surface energy is greater than the second surface energy, and the second surface energy is greater than the first surface energy, and wherein the fluid transport layer is a knit textile material comprising a first yarn forming a plurality of interlocking loops and at least one effect yarn tucked into the interlocking loops formed by the first yarn, wherein the plurality of interlocking loops formed by the first yarn provide the second surface of the fluid transport layer, and wherein the first yarn is more hydrophilic than the effect yarn.

2. The composite article of claim 1, wherein the first yarn comprises a polyamide and the effect yarn comprises a polyester.

3. The composite article of claim 2, wherein the fluid transport layer further comprises one or more elastomeric yarns.

4. The composite article of claim 1, wherein the composite article further comprises an antimicrobial agent.

5. The composite article of claim 1, wherein the fluid transport layer further comprises a coating applied thereto, and wherein the coating comprises an antimicrobial agent and a binder.

6. The composite article of claim 1, wherein the third surface energy is about 105% or more of the second surface energy.

7. The composite article of claim 1, wherein the fluid retentive layer is selected from the group consisting of foams, textile materials, alginates, superabsorbent polymers, gels, and combinations thereof.

8. The composite article of claim 7, wherein the fluid retentive layer comprises a foam.

9. The composite article of claim 8, wherein the fluid retentive layer comprises a polyester-based polyurethane foam.

10. The composite article of claim 1, wherein the composite article further comprises a hot-melt adhesive disposed between the second surface of the fluid transport layer and the first surface of the fluid retentive layer.

11. The composite article of claim 10, wherein the hot-melt adhesive is a polyamide adhesive web.

12. The composite article of claim 1, wherein the moisture vapor permeable film is a polyurethane film comprising a polyurethane polymer selected from the group consisting of polyether-based polyurethanes, polyester-based polyurethanes, and combinations thereof.

13. A wound dressing comprising:
(a) a fluid transport layer, the fluid transport layer having a first surface and a second surface, the first surface of the fluid transport layer providing a wound contacting surface having a first surface energy, and the second surface of the fluid transport layer having a second surface energy,
(b) a fluid retentive layer, the fluid retentive layer having a first surface and a second surface, the first surface of the fluid retentive layer having a third surface energy, and the fluid retentive layer being positioned so that the first surface layer of the fluid retentive layer is adjacent to the second surface of the fluid transport layer; and
(c) a moisture vapor permeable film, the moisture vapor permeable film being positioned so that it is adjacent to the second surface of the fluid retentive layer, the moisture vapor permeable film exhibiting a moisture vapor transmission rate (MVTR) of about 500 $g/m^2/24$ hr or more;

wherein the third surface energy is greater than the second surface energy, and the second surface energy is greater than the first surface energy, and wherein the fluid transport layer is a knit textile material comprising a first yarn forming a plurality of interlocking loops and at least one effect yarn tucked into the interlocking loops formed by the first yarn, wherein the plurality of interlocking loops formed by the first yarn provide the second surface of the fluid transport layer, and wherein the first yarn is more hydrophilic than the effect yarn.

* * * * *